(12) United States Patent
Marshall

(10) Patent No.: US 11,033,158 B1
(45) Date of Patent: Jun. 15, 2021

(54) PORTABLE URINAL TRAINING SYSTEM AND METHOD OF USE

(71) Applicant: Jesse Marshall, Dallas, TX (US)

(72) Inventor: Jesse Marshall, Dallas, TX (US)

( * ) Notice: Subject to any disclaimer, the term of this patent is extended or adjusted under 35 U.S.C. 154(b) by 0 days.

(21) Appl. No.: 16/524,485

(22) Filed: Jul. 29, 2019

(51) Int. Cl.
*A47K 11/06* (2006.01)
*A47K 13/06* (2006.01)
*G09B 19/00* (2006.01)
*A61F 5/451* (2006.01)

(52) U.S. Cl.
CPC ............. *A47K 11/06* (2013.01); *A47K 13/06* (2013.01); *G09B 19/00* (2013.01); *A61F 5/451* (2013.01)

(58) Field of Classification Search
CPC .................................................. A47K 11/06
USPC ...... 4/114.1, 144.1, 458, 449, 301; 600/573; 604/327
See application file for complete search history.

(56) References Cited

U.S. PATENT DOCUMENTS

| | | | | |
|---|---|---|---|---|
| 1,954,448 A * | 4/1934 | Hackett | ................. | A47K 13/00 40/299.01 |
| 2,769,982 A * | 11/1956 | Gossett | ................. | A47K 11/12 4/144.1 |
| D276,361 S * | 11/1984 | Hyman, Sr. | ............ | A47K 11/12 D23/297 |
| 4,785,483 A * | 11/1988 | Wise | ...................... | A47K 11/04 296/65.07 |
| 5,388,279 A * | 2/1995 | Rasmussen | ............ | A47K 11/12 4/144.1 |
| D379,407 S * | 5/1997 | Liu | ......................... | A47K 11/12 D21/428 |
| 5,822,804 A * | 10/1998 | Hauflaire | ................ | A47K 11/12 4/144.1 |
| 6,079,057 A * | 6/2000 | Mette | ...................... | E03D 1/003 4/342 |
| 7,412,732 B1 * | 8/2008 | Leonard | .................... | E03D 9/00 4/300.3 |
| 7,461,411 B2 * | 12/2008 | Wolf | ....................... | A47K 13/24 4/239 |
| D766,406 S * | 9/2016 | Hooker | .................. | A47K 11/12 D23/302 |
| 2002/0020006 A1 * | 2/2002 | Mason, Jr. | ............. | A47K 11/12 4/144.1 |
| 2008/0052810 A1 * | 3/2008 | Zeeb | ...................... | A47K 11/12 4/144.1 |
| 2008/0184470 A1 * | 8/2008 | Veroni | ................... | A47K 11/06 4/300.3 |
| 2009/0145340 A1 * | 6/2009 | Parvizian | ............... | A47C 16/02 108/137 |
| 2009/0320198 A1 * | 12/2009 | Yefremov | ............. | A47K 13/24 4/300.3 |
| 2011/0061972 A1 * | 3/2011 | Parvizian | ............... | A47C 12/00 182/35 |
| 2012/0131740 A1 * | 5/2012 | Rone | ...................... | A47K 13/14 4/245.3 |

(Continued)

*Primary Examiner* — Lori L Baker
(74) *Attorney, Agent, or Firm* — Richard Eldredge; Leavitt Eldredge Law Firm

(57) ABSTRACT

A urinal training system includes a base having a first side wall and a second side wall and a bottom floor extending therebetween; a top pivotally attached to the base, the top having a top edge, a first side, a second side, and a back wall extending therebetween; and a urinal apparatus embedded within the back wall of the top; the bottom floor provides a place to stand on while using the urinal apparatus.

6 Claims, 5 Drawing Sheets

(56) References Cited

U.S. PATENT DOCUMENTS

2015/0238058 A1\* 8/2015 Couch .................. A47K 13/24
4/300.3

\* cited by examiner

PORTABLE URINAL TRAINING SYSTEM AND METHOD OF USE

BACKGROUND

1. Field of the Invention

The present invention relates generally to potty training systems for children, and more specifically, to a portable urinal training system that provides for a fun way to aid in potty training.

2. Description of Related Art

Potty training is a common activity among parents and can be time consuming and tedious. Parents may use small, portable toilets, training pull-ups, incentives, or a plurality of other devices and systems to try to train their children to use the toilet. This process can become frustrating for both parents and children, and accordingly, there is room for improvement in potty training systems to provide for a fun way to aid in the process.

It is an object of the present invention to provide a collapsible and transportable urinal training system that can include decorative imagery to help a child in their potty training journey.

DESCRIPTION OF THE DRAWINGS

The novel features believed characteristic of the embodiments of the present application are set forth in the appended claims. However, the embodiments themselves, as well as a preferred mode of use, and further objectives and advantages thereof, will best be understood by reference to the following detailed description when read in conjunction with the accompanying drawings, wherein:

Figure 1:
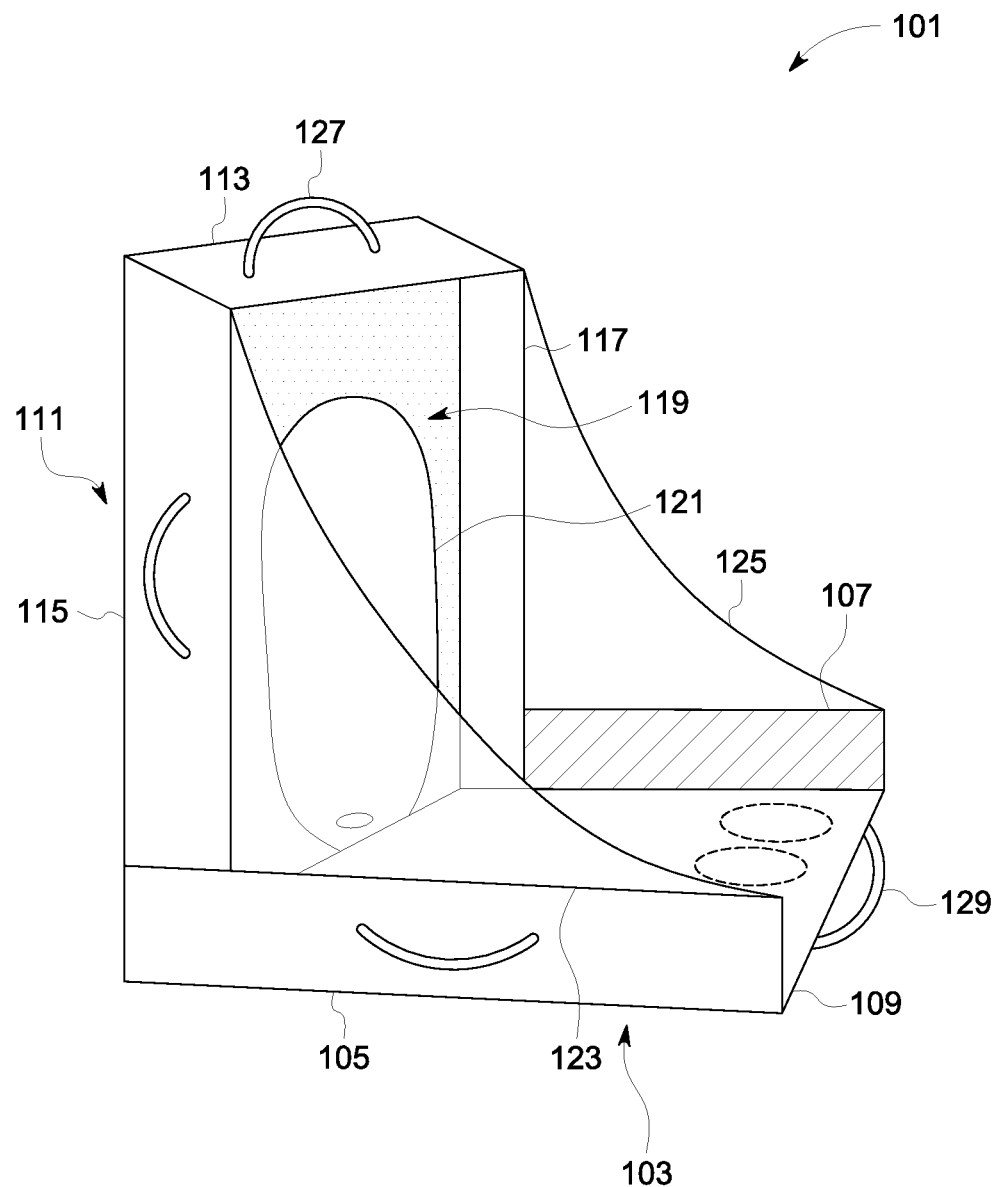
FIG. 1 is an isometric view of a portable urinal training system in accordance with a preferred embodiment of the present application.

While the system and method of use of the present application is susceptible to various modifications and alternative forms, specific embodiments thereof have been shown by way of example in the drawings and are herein described in detail. It should be understood, however, that the description herein of specific embodiments is not intended to limit the invention to the particular embodiment disclosed, but on the contrary, the intention is to cover all modifications, equivalents, and alternatives falling within the spirit and scope of the present application as defined by the appended claims.

DETAILED DESCRIPTION OF THE PREFERRED EMBODIMENT

Illustrative embodiments of the system and method of use of the present application are provided below. It will of course be appreciated that in the development of any actual embodiment, numerous implementation-specific decisions will be made to achieve the developer's specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

The system and method of use in accordance with the present application overcomes one or more of the above-discussed problems commonly associated with conventional potty training systems. Specifically, the present invention provides for a portable urinal training that is fun for the child and further aids in teaching the child how to properly aim. These and other unique features of the system and method of use are discussed below and illustrated in the accompanying drawings.

The system and method of use will be understood, both as to its structure and operation, from the accompanying drawings, taken in conjunction with the accompanying description. Several embodiments of the system are presented herein. It should be understood that various components, parts, and features of the different embodiments may be combined together and/or interchanged with one another, all of which are within the scope of the present application, even though not all variations and particular embodiments are shown in the drawings. It should also be understood that the mixing and matching of features, elements, and/or functions between various embodiments is expressly contemplated herein so that one of ordinary skill in the art would appreciate from this disclosure that the features, elements, and/or functions of one embodiment may be incorporated into another embodiment as appropriate, unless described otherwise.

The preferred embodiment herein described is not intended to be exhaustive or to limit the invention to the precise form disclosed. It is chosen and described to explain the principles of the invention and its application and practical use to enable others skilled in the art to follow its teachings.

Figure 2:
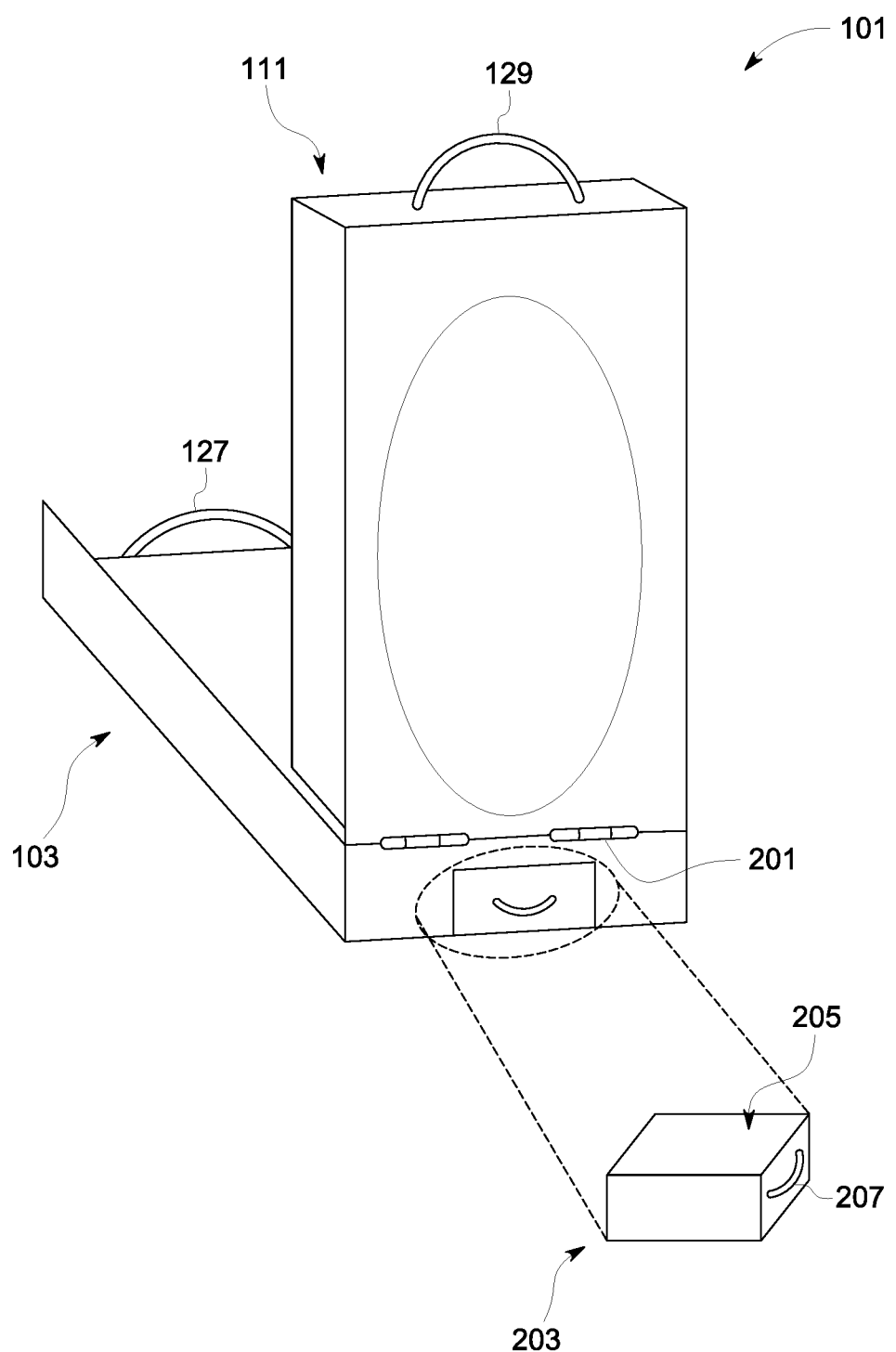
FIG. 2 is an isometric back view of the system of FIG. 1.

Referring now to the drawings wherein like reference characters identify corresponding or similar elements throughout the several views, FIGS. 1 and 2 depict views of a portable urinal training system 101 in accordance with a preferred embodiment of the present application. It will be appreciated that system 101 overcomes one or more of the above-listed problems commonly associated with conventional potty training systems.

In the contemplated embodiment, system 101 includes a base 103 having a having a first side wall 105 and a second side wall 107 and a bottom floor 109 extending therebetween. In the preferred embodiment, a top 111 is pivotally attached to the base 103 via one or more hinges 201, thereby providing a means for the apparatus to be folded together for transport. In the preferred embodiment, the top 111 having a top edge 113, a first side 115, a second side 117, and a back wall 119 extending therebetween.

System 101 further comprises a urinal apparatus 121 embedded within the back wall 119 of the top 111, wherein the bottom floor 109 provides a place to stand on while using the urinal apparatus 121.

In some embodiments, the system further includes a first shield 123 and a second shield 125 attached to the top and the bottom on opposite sides, the shields providing for protection against leaks and mess from the use of the urinal system. In the preferred embodiment, the shields are composed of a flexible material, thereby allowing for the shields to fold down as the apparatus is closed. As further shown, the system 201 can include handles 127, 129 that provide for portability of the system. It should be appreciated that the handles can be placed along the sides, top, and end as desired. This feature is important for allowing the parent to transport the system as needed.

As shown in FIG. 2, the system can further include a removable drawer 203 slidingly engaged the top 111 and in fluid communication with the urinal apparatus. It should be appreciated that the removable drawer 203 includes an interior area 205 to collect urine for removal and cleaning. In addition, as shown, the drawer 203 can include a handle 207.

Figure 3:
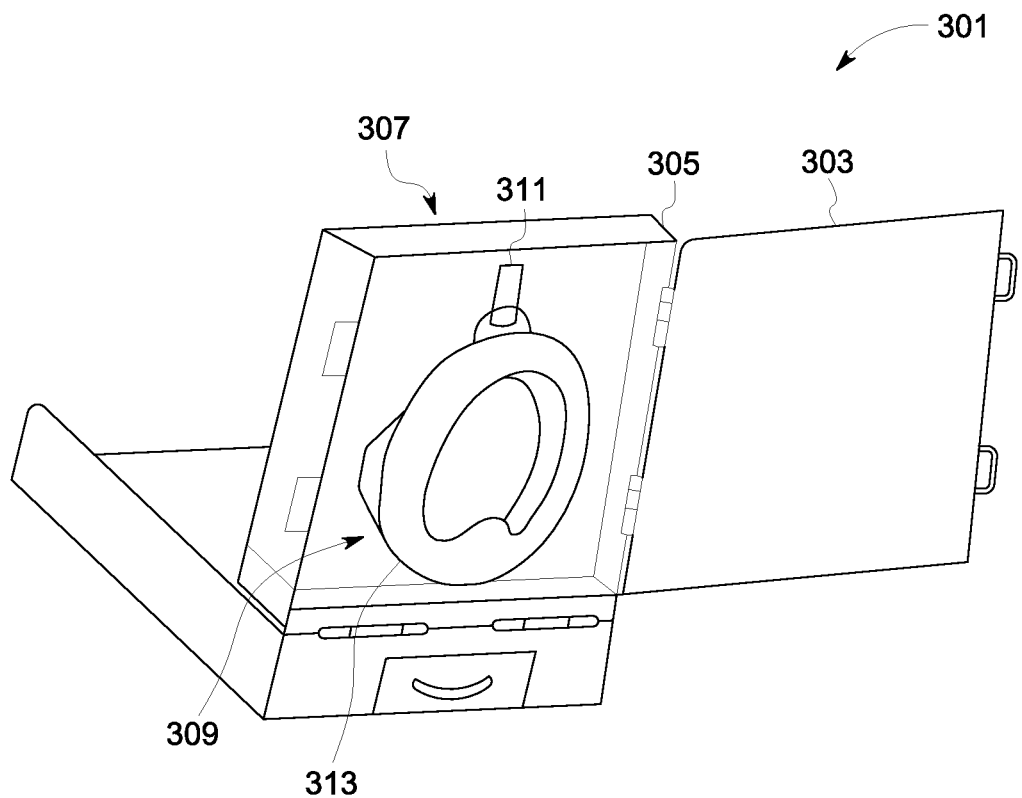
FIG. 3 is an isometric back view of an alternative embodiment of a portable urinal training system in accordance with the present application.
Figure 4:
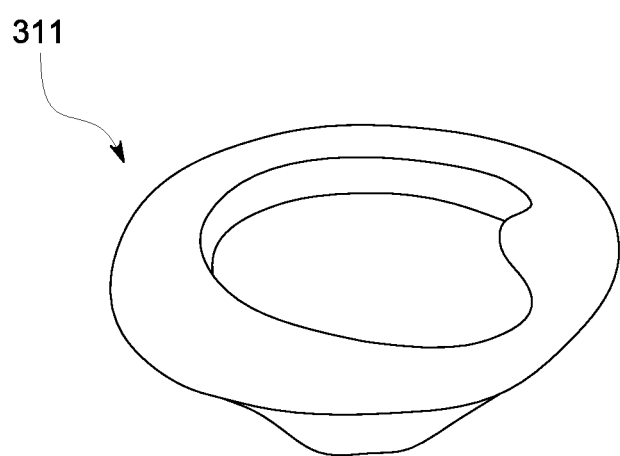
FIG. 4 is an isometric view of a training toilet of FIG. 3.

In FIGS. 3 and 4, an alternative embodiment of a portable urinal training system 301 is shown. System 301 can include all of the features discussed above, and further includes a back door 303 pivotally attached to a first side 305 of the top 307, wherein the door 303 provides access to an interior area 309. In this embodiment, a hook 311 is positioned within the interior area and configured to receive and store a training toilet 313. This allows for a parent to remove the training toilet 313 for use with a toilet as needed. An exemplary embodiment of training toilet 313 is shown in FIG. 4, however, it should be appreciated that the precise configuration can vary.

It should be appreciated that one of the unique features believed characteristic of the present application is the configuration of the system to allow for portability and improved urinal training for children.

Figure 5:
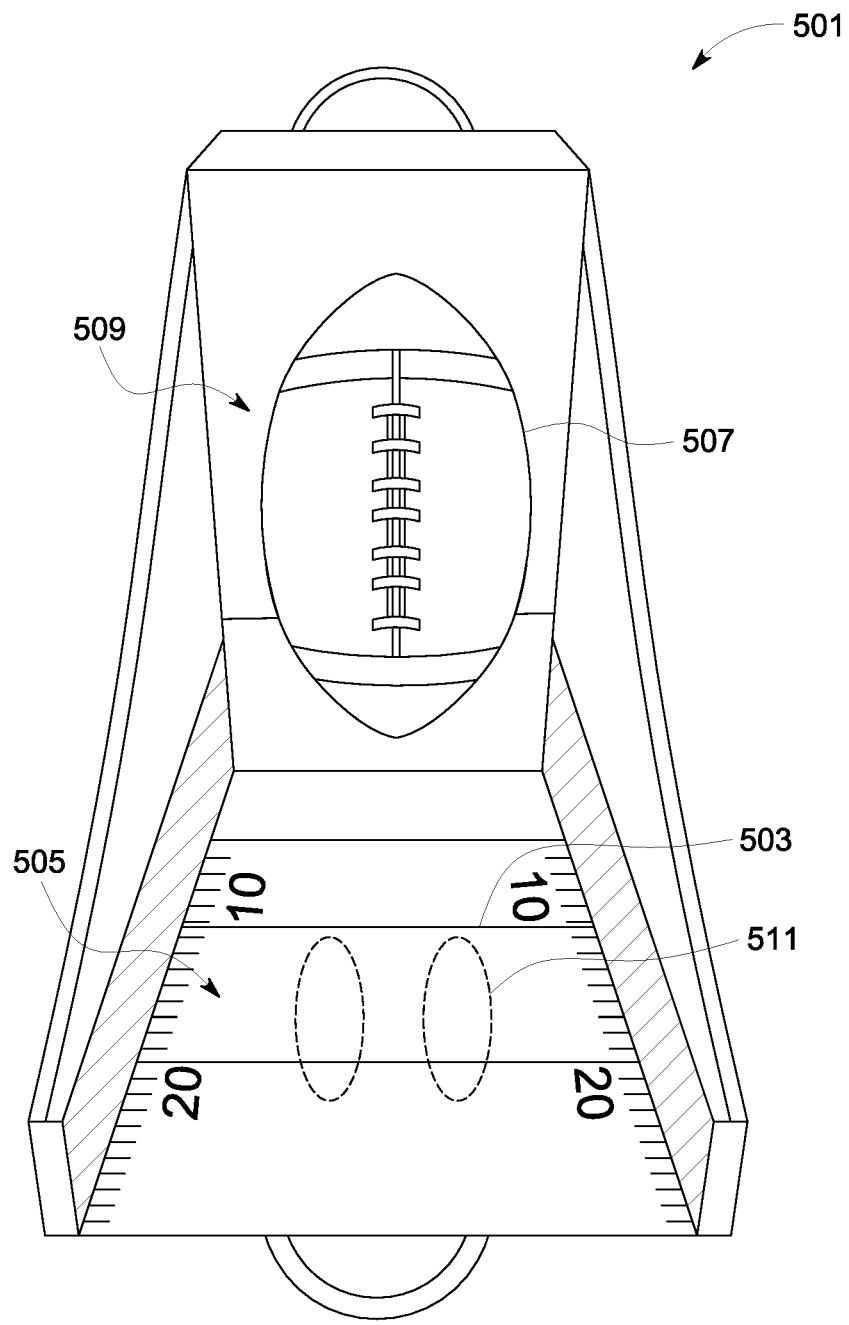
FIG. 5 is a front view of an alternative embodiment of a portable urinal training system in accordance with the present application.

In FIG. 5, yet another alternative embodiment or a portable urinal training system 501 is shown, being similar in form and function to system 201 and including all of the features discussed herein. In this embodiment, a first decorative insignia 503 is printed on a top surface 505 of the base and a second decorative insignia 507 printed on a front surface 509 of the top. As shown, the decorative insignia can turn system 501 into a game, such as providing the child with a goal to aim for. As further show, the system can include particular markings 511 to indicate to the child where to stand. It should be appreciated that although football is shown as the example, other sports, activities, or decorations could be used.

Figure 6:
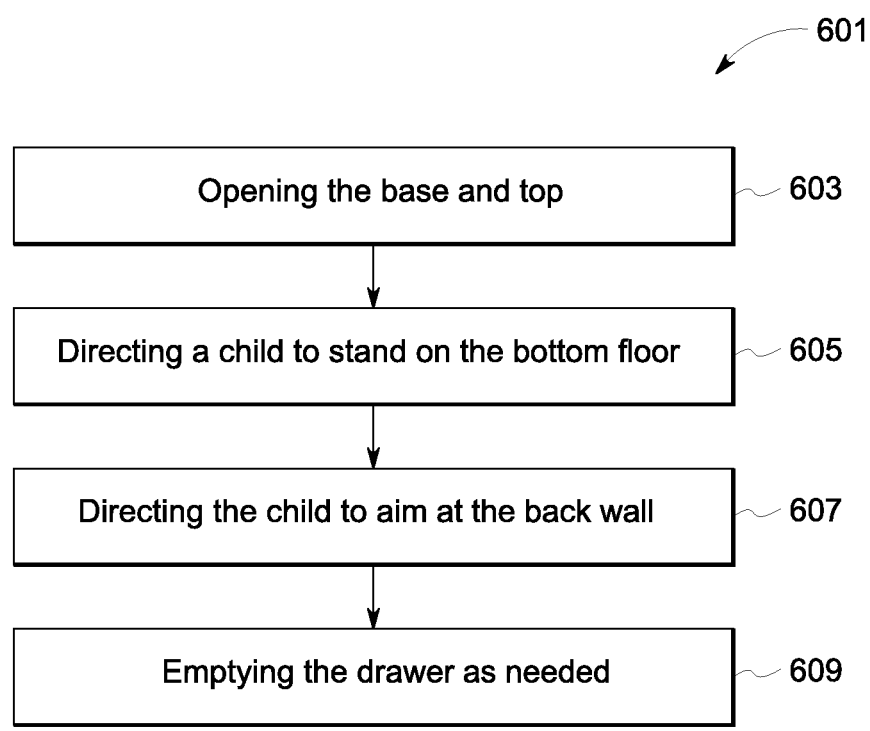
FIG. 6 is a flowchart of the method of use of the present invention.

In FIG. 6, a flowchart 601 depicts the method of use of the system. During use, the top and base are positioned in an open configuration, and a child can be directed to stand on the bottom floor and aim at the back wall, as shown with boxes 603, 605, 607. The user can then empty the drawer as needed, as shown with box 609.

The particular embodiments disclosed above are illustrative only, as the embodiments may be modified and practiced in different but equivalent manners apparent to those skilled in the art having the benefit of the teachings herein. It is therefore evident that the particular embodiments disclosed above may be altered or modified, and all such variations are considered within the scope and spirit of the application. Accordingly, the protection sought herein is as set forth in the description. Although the present embodiments are shown above, they are not limited to just these embodiments, but are amenable to various changes and modifications without departing from the spirit thereof.

What is claimed is:

1. A urinal training system, comprising:
 a base having a first side wall and a second side wall and a rectangular bottom floor extending therebetween;
 a top pivotally attached to the base, the top having a top edge, a first side, a second side, and a rectangular back wall extending therebetween;
 a urinal apparatus embedded solely within the back wall of the top;
 a first flexible shield attached to the first side of the top and attached to the base at the first side wall;
 a second flexible shield attached to the second side of the top and attached to the base at the second side; and
 a drawer removably secured to a back of the base, the drawer is in fluid communication with the urinal apparatus and removable from the back of the base;
 wherein the bottom floor provides a place to stand on while using the urinal apparatus.

2. The system of claim 1, further comprising:
 a decorative insignia printed on a top surface of the bottom floor; and
 a second decorative insignia printed on a front surface of the back wall.

3. The system of claim 1, further comprising:
 a first handle attached to the base; and
 a second handle attached to the top.

4. The system of claim 1, further comprising:
 a back door pivotally attached to the first side of the top;
 an interior area within the top that is accessible via the back door; and a hook positioned within the interior area.

5. The system of claim 4, further comprising:
 a training toilet removably secured to the hook within the interior area.

6. A method of toilet training, the method comprising:
 providing the system of claim 1;
 directing a child to stand on the bottom floor; and directing the child to aim at the urinal apparatus.

* * * * *